United States Patent
Stuczynski et al.

(10) Patent No.: US 6,475,932 B1
(45) Date of Patent: Nov. 5, 2002

(54) HIGH STRENGTH THROUGH-BONDING TECHNIQUE FOR ELASTOMERIC LAMINATES

(75) Inventors: Russell P. Stuczynski, South Milwaukee, WI (US); Diane M. Strelow, Waukesha, WI (US); James D. Carper, Waukesha, WI (US)

(73) Assignee: Ato Findley, Inc., Wauwatosa, WI (US)

( * ) Notice: Subject to any disclaimer, the term of this patent is extended or adjusted under 35 U.S.C. 154(b) by 0 days.

(21) Appl. No.: 09/240,738

(22) Filed: Jan. 29, 1999

(51) Int. Cl.⁷ .............................. B32B 5/26; B32B 3/10
(52) U.S. Cl. ............................ 442/36; 442/35; 442/46; 442/49; 442/149; 442/150; 442/328; 428/131; 428/134; 428/136; 428/137; 428/192; 428/194
(58) Field of Search .............................. 442/36, 35, 46, 442/49, 149, 150, 328; 428/192, 194, 131, 134, 136, 137

(56) References Cited

U.S. PATENT DOCUMENTS

| | | | |
|---|---|---|---|
| 4,229,473 A | 10/1980 | Elber | 428/113 |
| 4,581,269 A | 4/1986 | Tilman | 428/62 |
| 4,587,175 A | 5/1986 | Akao | 428/596 |
| 4,863,779 A | 9/1989 | Daponte | 428/152 |
| 5,804,286 A | * 9/1998 | Quantrille et al. | 428/198 |
| 5,853,881 A | 12/1998 | Estey et al. | 428/373 |
| 5,861,074 A | 1/1999 | Wu | 156/229 |
| 6,048,603 A | * 4/2000 | Ruppel et al. | 428/195 |

FOREIGN PATENT DOCUMENTS

| | | |
|---|---|---|
| EP | 0 420 256 | 3/1991 |
| WO | WO 96/21562 | 7/1996 |
| WO | WO 96/38620 | 12/1996 |
| WO | WO 98/0230 | 1/1998 |
| WO | WO 98/10919 | 3/1998 |

* cited by examiner

*Primary Examiner*—Elizabeth M. Cole
*Assistant Examiner*—Ula C. Ruddock
(74) *Attorney, Agent, or Firm*—Andrus, Sceales, Starke & Sawall, LLP

(57) ABSTRACT

The fabrication of multi-layered laminated structures involves a high strength through-bonding technique. In its preferred embodiment, the structure is a nonwoven trilaminate structure which has outer layers of nonwoven material, and an inner elastomeric layer which has a plurality of openings therethrough, (e.g., an elastomeric mesh). During fabrication, beads of through-bonding adhesive (e.g., oil resistant, polybutylene-based hot melt adhesive) is applied to at least one of the nonwoven webs. The inner elastomeric mesh web and the two outer nonwoven webs are then aligned and fed into a compression nip. The compression nip compresses the webs together to obtain intimate contact of the two outer nonwoven webs through the openings in the inner elastomeric mesh web. In the resultant trilaminate web, the inner elastomeric mesh layer is mechanically secured within the trilaminate structure via the through-bonding even if bonds directly between the inner elastomeric mesh and either of the outer nonwoven webs fail. Preferably, the beads of through-bonding adhesive are applied only in regions of the web where strength enhancement is desired to insure the integrity and durability of the finished product, e.g. adjacent the longitudinal edges of the finished nonwoven trilaminate product.

28 Claims, 4 Drawing Sheets

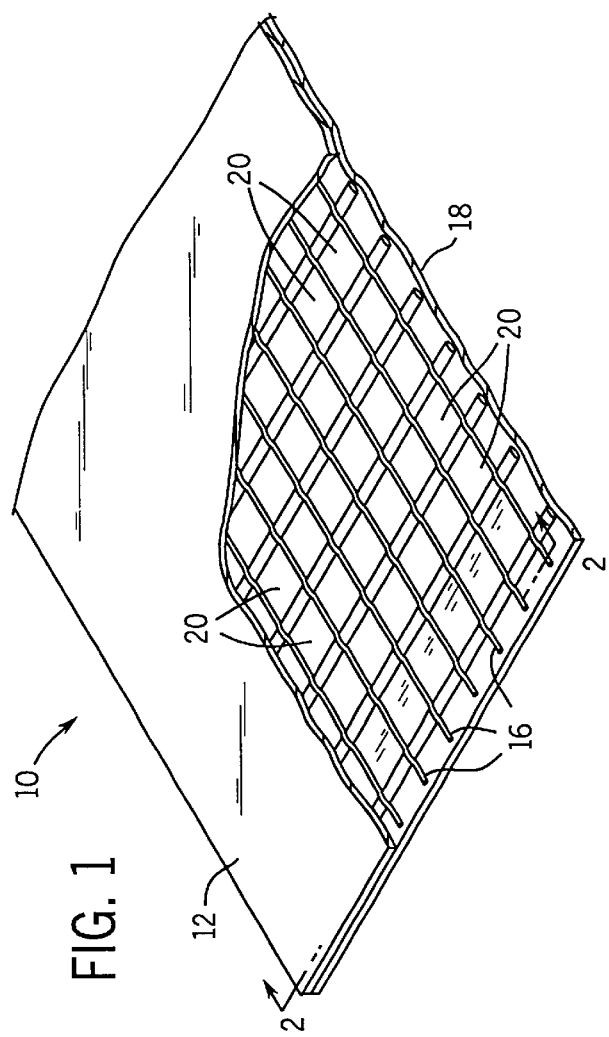
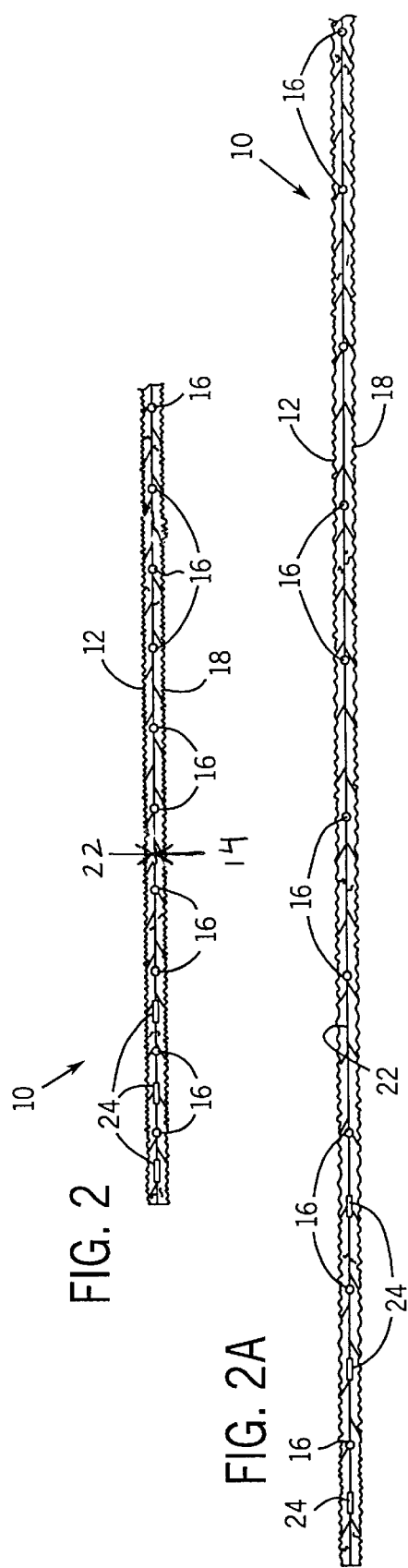

HIGH STRENGTH THROUGH-BONDING TECHNIQUE FOR ELASTOMERIC LAMINATES

FIELD OF THE INVENTION

The invention relates to laminated structures that are useful in the construction of disposable articles, e.g. diapers, etc. In particular, the invention relates to a high strength, through-bonding technique that enhances the strength and durability of stretchable laminates.

BACKGROUND OF THE INVENTION

Many commercially available disposable articles include laminated components which are breathable and stretchable, for example absorbent articles like disposable diapers for infants and undergarments for incontinent adults use stretchable side panels. Many, if not most, of these disposable articles use layers of nonwoven material. Other products which use nonwoven laminates include bandages, body wraps, and the like.

Several types of nonwoven fabrics are known in the art. In general, nonwoven fabrics contain fibers of polyethylene, polypropylene, polyethylene terephalate, nylon, or rayon and are joined in any number of ways for example adhesives, thermal bonding, felting, or other methods known in the art. Thermally bonded nonwoven polypropylene is particularly prevalent in disposable articles. Thermally bonded nonwoven polypropylene is breathable and has a soft, cloth-like feel which is particularly suitable for these applications.

The assignee of this application has been involved in the development of various adhesives for use in nonwoven laminated structures, e.g. see copending U.S. patent application Ser. No. 08/632,117 entitled "Oil Resistant Polybutylene Based Hot Melt Adhesive" filed on Apr. 15, 1996 by Bonnie M. Harris and Monina Kanderski; and U.S. patent application Ser. No. 08/914,523 entitled "Hot Melt Adhesive Having a High Acid Number for Disposable Soft Goods", filed on Aug. 9, 1997 by Mark D. Alper and Diane Strelow, both incorporated herein by reference. As discussed in the above incorporated patent applications, it is difficult to find adhesives that are effective for bonding nonwoven material to the elastomeric films or meshes which are desirable for use in nonwoven laminate structures. Some elastomeric films or mesh webs (e.g., oil resistant materials or materials embodying incompatible process aids) are simply difficult to laminate with nonwoven fabric. In addition, effective and durable bonding to elastomeric film or mesh is particularly difficult because of the mechanical stresses put on the bonds when the laminated structure is repeatedly stretched.

The following discussion regarding elastomeric films and meshes is added to provide a more complete explanation of some of the difficulties encountered when fabricating laminated structures with commercially available elastomeric films or meshes.

Commercially available elastomeric films and meshes are typically manufactured from A-B-A block copolymers such as styrene-butadiene-styrene (SBS), styrene-isoprene-styrene (SIS), styrene-ethylene/butylene-styrene, as well as other polyolefins such as, but not limited to, ethylene vinyl acetate (EVA), and low density polyethylene (LDPE). These elastomeric materials typically include about 20% to about 30%, by weight, of the elastomeric block copolymers, and about 20% to about 30%, by weight, of other polyolefins, or ethylene vinyl acetate. An example of these films and the specifics of their composition can be found in U.S. Pat. No. 4,476,180. Once these elastomeric webs are formulated and extruded, the webs can be very tacky. The tackiness makes it difficult to process the web on the extrusion line, and in subsequent converting equipment. To address problems associated with the tackiness of the elastomeric web, manufacturers of the elastomeric webs usually incorporate a relatively high amount of slip agent into their formulations. For example, fatty acid amides having the formula $CH_3$—R—CO—$NH_2$ are commonly used as slip agents. The letter R is a chain of repeating—$CH_2$—units typically about 12 to 24 carbon atoms in length. The most commonly used fatty acid amide is Erucamide. It is commercially available under the trade name Kemamide B from the Humko-Sheffield Chemical Company. This particular slip agent has a carbon chain which is 22 units long, a molecular weight of about 337.6, and a capillary melting point of about 82° C.

The slip agents incorporated into the elastomeric films and meshes have caused significant problems for prior art hot melt adhesives which are commonly used in the production of nonwoven laminates. In particular, it is believed that the slip agents become mobile, under specific environmental circumstances, or are otherwise incompatible with the polymers used in the elastomeric films or meshes; and, these two factors combine to cause the slip agents to migrate to, or otherwise to become deposited on, or "bloom" to, the exterior surface of the film or mesh. The slip agents have a waxy nature, and they act as a lubricant once they bloom to the surface of the film or mesh. For the manufacturers of elastomeric film and meshes, this provides two valuable benefits. The first benefit is that the presence of the waxy layer on the exterior surface of the film or mesh helps prevent adjacent layers of film from adhering thereto (known in the industry as "blocking") when it is placed into a roll form. The second benefit is that the waxy layer acts as a lubricant, thereby facilitating the use of the film when it is unwound, and later processed over rollers, guides, etc. during subsequent converting and/or processing.

While the slip agents referred to above facilitate and even enhance the use of these synthetic films and meshes in manufacturing, the slip agents which migrate to the exterior surface of the film or mesh appear to destroy, or substantially weaken bonds of prior art adhesives. The amount of slip agent present in the films currently in commercial production ranges from about 0.1% to 1%, by weight, although some films currently in production have as much as 4.5%, by weight. A further disclosure of the use of slip agents in films or meshes can be found in U.S. Pat. Nos. 4,476,180, 4,977,014 and 4,714,735, all of which are incorporated by reference herein.

In view of the difficulty surrounding the application of hot melt adhesives to elastomeric films and meshes, the industry has long sought a hot melt adhesive composition which would effectively bind these elastomeric films and meshes to breathable materials, such as nonwoven webs.

SUMMARY OF THE INVENTION

In contrast to prior attempts to develop improved adhesives, the invention involves the use of a high strength through-bonding fabrication technique for elastomeric laminates. In its preferred embodiment, the laminated structure includes two outer layers of nonwoven material and an inner elastomeric layer laminated between the outer nonwoven layers. The inner elastomeric layer is preferably a mesh, and in accordance with the invention, must provide openings therethrough so that a bonding side of the first nonwoven outer layer is exposed through the openings to a bonding side of the second nonwoven outer layer. An A important aspect of the invention involves the use of through-bond adhesive to directly bond the first and second outer layers of nonwoven material to each other through at least some of the openings in the inner layer. The direct bonds between the nonwoven layers that occur through the openings in the elastomeric mesh mechanically secure the elastomeric mesh within the trilaminate structure. In many applications, it may also be desirable to provide adhesive for bonding the outer nonwoven layers directly to the elastomeric mesh. It is the direct bond, however, between the nonwoven layers that occurs through the openings in the elastomeric mesh that is primarily responsible for enhancing the durability of the nonwoven trilaminate structure.

In some nonwoven/elastomeric mesh trilaminates or like structures, the nonwoven layers are not stretchable in the machine direction, but are spreadable in the cross direction. The elastomeric mesh allows the trilaminate to stretch in the cross direction when the trilaminate is stretched, and returns the trilaminate to the relaxed position when the stretching ceases. In nonwoven trilaminate structures where the outer nonwoven layers are bonded directly to the elastomeric mesh, but not bonded to each other through openings in the mesh, repeated stretching tends to promote delamination. This is due to the inherent difficulties in bonding elastic materials. Using a through-bonding technique in accordance with the invention substantially eliminates this problem, even when there is repeated stretching.

The invention is not limited to nonwoven elastomeric mesh trilaminates. For example, the through-bonding technique improves durability of laminated structures using types of breathable material other than nonwoven. Further, the invention should not be limited to trilaminate (i.e., three ply) structures, inasmuch as the structure could contain additional layers in accordance with the invention.

In another aspect, the invention is a method of fabricating a breathable, stretchable laminated web on a laminating machine which receives the two webs of breathable material (e.g. nonwoven) and one web of the elastomeric material having a plurality of openings therethrough. The method facilitates effective through-bonding of the breathable layers through the openings in the elastomeric web. It involves feeding a first web of breathable material into the laminating machine. Separately from the first web of breathable material, a second web of breathable material is also fed into the laminating machine. In addition, the elastomeric web having a plurality of openings is also fed into the laminating machine. The webs are aligned with the elastomeric web placed between the webs of breathable material. Before the webs are completely aligned, through-bonding adhesive is applied on the bonding side of at least one of the webs of breathable material. The through-bonding adhesive is preferably applied in beads via a bead applicator, but could also be applied using other known methods. The adhesive must be applied, however, under conditions (e.g. temperature, viscosity, machine speed, compression force, etc.) sufficient to allow the through-bonding adhesive to flow through the openings in the elastomeric web and wet the bonding side of the other web of breathable material when the webs are aligned and subsequently compressed together. The preferred through-bonding adhesive is an oil resistant, polybutylene-based hot melt adhesive, although the invention can be implemented using other types of through-bonding adhesive. After the adhesive has been applied and the webs have been aligned, the webs pass through a compression nip to achieve intimate contact between the wetted bonding sides of the first and second webs of breathable material. It is preferred that the compression force be at least 50 pounds per lineal inch. The preferred compression nip is formed by a hard roller (e.g. steel) and a resilient roller (e.g. rubber). Pneumatic cylinders can be used to control the compression force applied at the compression nip. It is important that there be a sufficient amount of through-bonding adhesive to wet the bonding side of both webs of breathable material through the openings in the elastomeric web, and that there be sufficient compression to insure intimate contact between the wetted bonding sides of the webs of breathable material to facilitate proper bonding. The laminated web can then be longitudinally sliced and perforated in the machine direction as is known in the art to create tear lines and form a plurality of laminated webs.

It is preferred that the beads of through-bonding adhesive be applied to the bonding side of one of the webs of breathable material, but not directly on the second web of breathable material. Instead, a sprayed-on adhesive is preferably applied on the second web of breathable material. Thereafter, the elastomeric web is aligned and brought into contact with the second web of breathable material and adhered thereto via the sprayed-on adhesive. Thereafter, it is preferred to spray-on additional adhesive. The resulting web (i.e. the second web of breathable material with the elastomeric web adhered thereto) is then aligned with the first web of breathable material to which the beads of through-bonding adhesive have been applied. The aligned webs then pass through the compression nip as described above.

The preferred bead applicator has an adhesive plenum and a plurality of adhesive application nozzles that may or may not be in contact with the bonding side of the first web of breathable material. In order to facilitate application of a sufficient amount of through-bonding adhesive, the nozzles can be arranged in a series of diagonal rows. Inasmuch as a relatively significant amount of through-bonding adhesive should to be applied to reliably secure the inner elastomeric layer within the trilaminate structure, the amount of through-bonding adhesive applied during fabrication should be selected carefully, otherwise the finished product may become overly stiff. In many applications, it may be desirable to apply the through-bonding adhesive only along selected portions of the web (e.g. along the longitudinal edges of the spliced laminated webs), thereby mechanically securing the inner elastomeric web within the trilaminate structure without creating an overly stiff finished product.

As should be apparent to those skilled in the art, the high strength through-bonding technique improves the durability of finished products using the laminated structure, without significantly compromising line speed of the lamination machine. Importantly, the through-bonding process and adhesive chemistry overcomes adhesion difficulties caused by process aids (e.g. slip agents, oils, etc.) on elastomeric film or mesh when fabricating laminated structures. The invention is also likely to reduce costs associated with the development of new laminates. The invention eliminates the need, at least in some circumstances, to find a suitable adhesive to bond a nonwoven layer directly to an inner elastomeric layer as is typically necessary during the development of conventional laminated structures.

Other features and advantages of the invention should be apparent to those skilled in the art upon inspecting the following drawings and descriptions thereof.

BRIEF DESCRIPTION OF THE DRAWINGS

FIG. 1 is a perspective schematic view of a nonwoven trilaminate structure fabricated in accordance with the invention.

FIG. 2 is a cross-sectional view of a nonwoven trilaminate structure manufactured in accordance with the invention taken along line 2—2 in FIG. 1.

FIG. 2a is a view similar to FIG. 2 showing the nonwoven trilaminate structure being stretched.

DETAILED DESCRIPTION OF THE DRAWINGS

Figure 3:
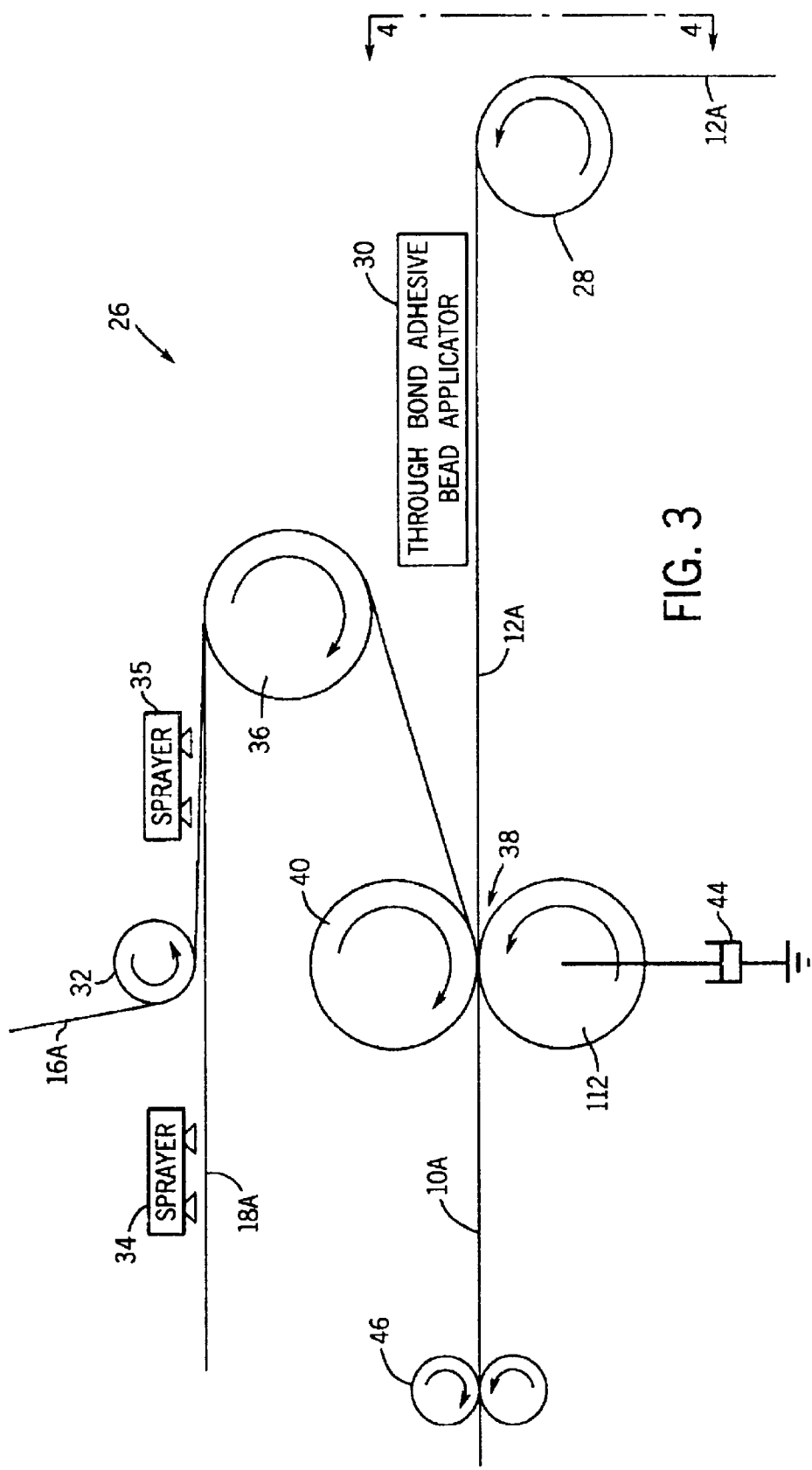
FIG. 3 is a schematic view illustrating a laminating machine that implements a high strength through-bonding technique in accordance with the invention.
Figure 4:
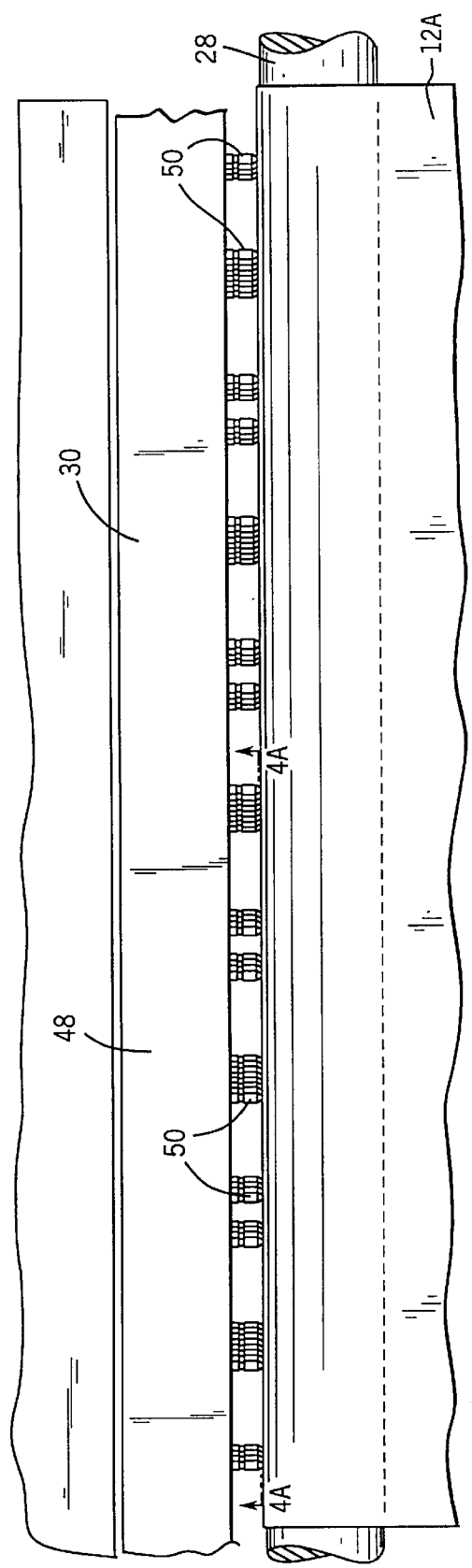
FIG. 4 is an elevational view showing an adhesive bead applicator applying beads of through-bonding adhesive to a bonding side of a first outer nonwoven web.
Figure 5:
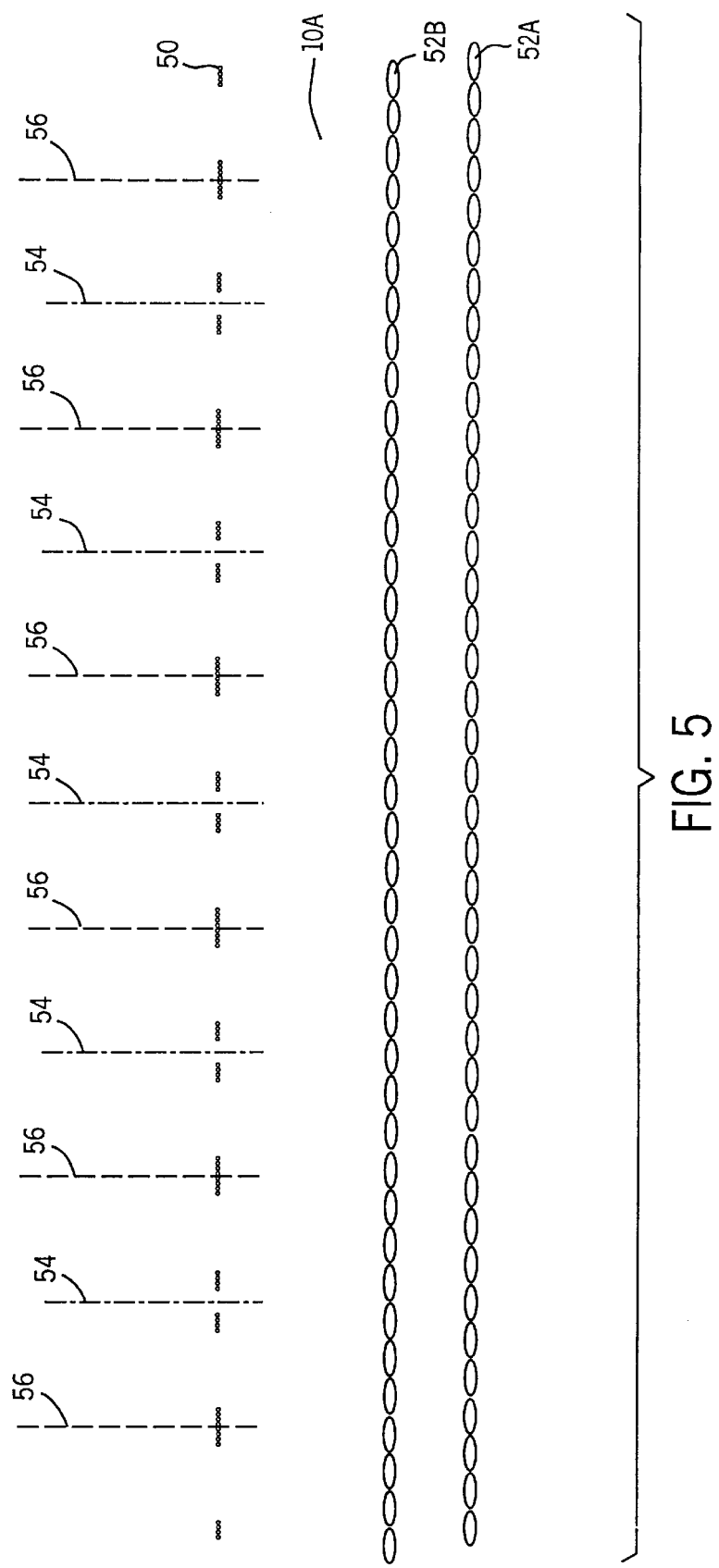
FIG. 5 is a schematic view illustrating the preferred adhesive application pattern used when implementing the invention.

The drawings illustrate the best mode of carrying out the invention, however, it should be understood that the scope of the invention should not be limited to this preferred embodiment. FIGS. 1, 2 and 2a illustrate a nonwoven trilaminate structure 10 constructed in accordance with the preferred embodiment of the invention. FIGS. 3 through 5 relate to the preferred method of fabricating the nonwoven trilaminate structure 10.

Referring to FIG. 1, the nonwoven trilaminate structure 10 is formed from a first nonwoven layer 12 (i.e., a first layer of breathable material), an inner elastomeric layer 16, and a second nonwoven layer 18 (i.e., a second layer of breathable material). The elastomeric layer 16 is laminated between the first 12 and second 18 nonwoven layers. The elastomeric layer includes a plurality of openings 20 therethrough, and is preferably a stretchable elastomeric mesh. The preferred elastomeric mesh has a thickness of 0.025 inches, although other sizes of elastomeric mesh can be used in accordance with the invention. The trilaminate structure 10 can be incorporated into a variety of products when a soft, durable, breathable and elastic panel is desired. Examples of such products includes diapers, incontinence products, bandages, body wraps and the like.

In the preferred embodiment of the invention, the nonwoven layers 12, 18 are thermal bonded polypropylene. One example of a suitable nonwoven material has a basis weight of 63 gm per square meter, a tensile strength in the machine direction of 7000 gm per inch, and in a cross direction of 425 gm per inch. Many other types of nonwoven materials can also be used in accordance with the invention.

Referring to FIGS. 2 and 2a, the first outer nonwoven layer 12 has a bonding side 14. The second outer nonwoven layer 18 also has a bonding side 22. Through-bonding adhesive 24 is applied to the trilaminate structure 10 and directly bonds the bonding side 14 of the first nonwoven layer 12 to the bonding side 22 of the second nonwoven layer 18 through openings 20 in the elastomeric layer 16. It is not necessary when implementing the invention to apply the through-bonding adhesive 24 at all the openings 20 through the inner layer 16. The preferred through-bonding adhesive is a polybutylene based hot melt adhesive as disclosed in pending U.S. patent application Ser. No. 08/632,117 entitled "Oil Resistant Polybutylene Based Hot Melt Adhesive" by Bonnie M. Harris and Monina Kanderski filed on Apr. 15, 1996 which has previously been incorporated herein by reference. Other adhesives may also be suitable for use as the through-bonding adhesive. For example, the adhesives manufactured by Ato Findley, Inc. of Wauwatosa, Wis. and marketed under the name H9282F should be satisfactory.

Although not illustrated on FIG. 2 and not necessarily required for implementing the invention, it may be desirable to apply another adhesive on either (or both) of the nonwoven layers 12, 18 to provide adherence directly to the inner layer 16. Preferably, this additional adhesive is sprayed-on. The preferred sprayed-on adhesive is an elastomeric, pressure sensitive adhesive such as the adhesive marketed under the name H2120 by Ato Findley, Inc. of Wauwatosa, Wis., the assignee of the present application.

The through-bonding adhesive 24 secures the respective bonding sides 14, 22 of the outer nonwoven webs through the openings 20 in the inner elastomeric layer 16 such that the strands of the elastomeric layer 16 are mechanically secured in the nonwoven trilaminate structure 10 even if the direct bonds between the elastomeric layer 16 and either or both of the nonwoven layers 12, 18 fails. FIG. 2a schematically illustrates the nonwoven trilaminate structure 10 being stretched. The strands 16 of the inner elastomeric layer are not in general directly bonded to either of the outer nonwoven layers 12, 18, as shown in FIG. 2a. Nonetheless, the strands 16 of the elastomeric layer are mechanically secured within the structure 10 by the surrounding bonds 24 bonding the outer layers of nonwoven material through the openings 20 in the elastomeric layer 16, even when the laminated trilaminate structure is stretched.

In accordance with the invention, the average peel strength of the through-bonding 24 that occurs between the nonwoven outer layers 12, 18 is greater than the average peel strength of any bonds that may be present directly between the elastomeric layer 16 and either outer nonwoven layer 12, 18. In fact, tests by the assignee have shown that the peel strength of the bonds between the outer nonwoven layers 12, 18 through the openings 20 and the elastomeric layer 16 are likely to be in excess of two times greater than the peel strengths of bonds directly between the elastomeric layer 16 and either nonwoven outer layer 12, 18.

The preferred method of fabricating the nonwoven trilaminate structure 10 shown in FIGS. 1, 2 and 2a is now described in reference to FIGS. 3, 4, 4a and 5. Referring first in particular to FIG. 3, the nonwoven trilaminate 10A is fabricated in a laminating machine 26 which preferably includes the components shown schematically in FIG. 3. In FIG. 3, a first nonwoven web 12a is fed into the laminating machine from a nonwoven roll unwinder as is known in the art. The first nonwoven web passes over input roller 28 and is fed underneath a through-bonding adhesive bead applicator 30. The through-bonding adhesive bead applicator 30 applies beads of the through-bonding adhesive on the bonding side of the first nonwoven web 12a. A second nonwoven web 18a is also fed into the laminating machine 26. In addition, the elastomeric web 16a is fed into the laminating machine 26, and passes over roller 32 to align the elastomeric web 16a with the second nonwoven web 18a. If no machine direction stretch is desired, it is preferred that the elastomeric web 16a be fed to the laminating machine 26 at or near zero tension, otherwise the finished product can be distorted or deformed. Prior to introducing the elastomeric web 16a, a conventional adhesive is sprayed on the bonding side of the second nonwoven web 18a by sprayer 34. Subsequent to introducing the elastomeric web 16a, additional adhesive is sprayed-on by sprayer 35. One of the purposes of the sprayed-on adhesive is to bond the elastomeric web 16a directly to the bonding side of the second nonwoven web 18a which can be important for maintaining proper alignment of the elastomeric web 16a during the fabrication process. In the preferred machine 26, the sprayers 34 and 35 spray adhesive in spiral patterns on the nonwoven web 18a and the combination of the elastomeric web 16a and the nonwoven web 18a, as is shown in FIG. 5, (row 52a by sprayer 34 and row 52b by sprayer 35). Each row 52a, 52b is created by staggered rows of spiral patterns from the respective sprayer 34, 35 to ensure complete coverage of the sprayed-on adhesive. The sprayed-on adhesive is preferably selected to provide an effective bond between the nonwoven web 12a and elastomeric web 16a. As mentioned previously in connection with FIG. 1, the preferred adhesive is an elastomeric, pressure-sensitive adhesive, for example, Ato Findley adhesive H2120 in the preferred embodiment of the invention in which the inner web 16a is an elastomeric mesh and the outer nonwoven web 18a is a thermally bonded nonwoven polypropylene material.

The aligned second nonwoven web 18a and inner elastomeric mesh web 16a pass over alignment roll 36 and continue towards compression nip 38. In compression nip 38, the second nonwoven web 18a and elastomeric web 16a are compressed against the first nonwoven web 12a which has beads of through-bonding adhesive applied thereon. The aligned webs 12a, 16a and 18a are compressed together with a sufficient amount of compression force to obtain intimate contact of the wetted bonding side of the first nonwoven web 12a and the bonding side of the second nonwoven web 18a even though the inner elastomeric mesh web 16a is located therebetween. A compression force at compression nip 38 of approximately 50 pounds per lineal inch or greater has been found to be optimal for laminating the preferred nonwoven trilaminate structure 10 described in conjunction with FIGS. 1 and 2. Preferably, the compression nip 38 comprises a hard cylindrical roller 40 (e.g., a steel roller) and a resilient cylindrical roller 42 (e.g., a rubber roller). The compression rollers 40, 42 are preferably mounted to pneumatically controlled mounts on the laminating machine 26. One or more pneumatic cylinders 44 can be used to control the amount of compression at the compression nip 38. Depending on the specific trilaminate structure, the compression rollers 40, 42 at the nip 38 may or may not have a fixed minimum gap or clearance therebetween. It is important, however, that the amount of compression force at the nip 38 be selected so that the through-bonding adhesive on the bonding side of the first nonwoven web of 12a sufficiently wets the bonding side of the second nonwoven web 18a and initiates a secure bond therebetween through openings 20 in the inner elastomeric layer 16a. Downstream of the compression nip 38, the laminated web 10a can then be sliced and perforated longitudinally by roller dies 46 as is known in the art.

Figure 4A:
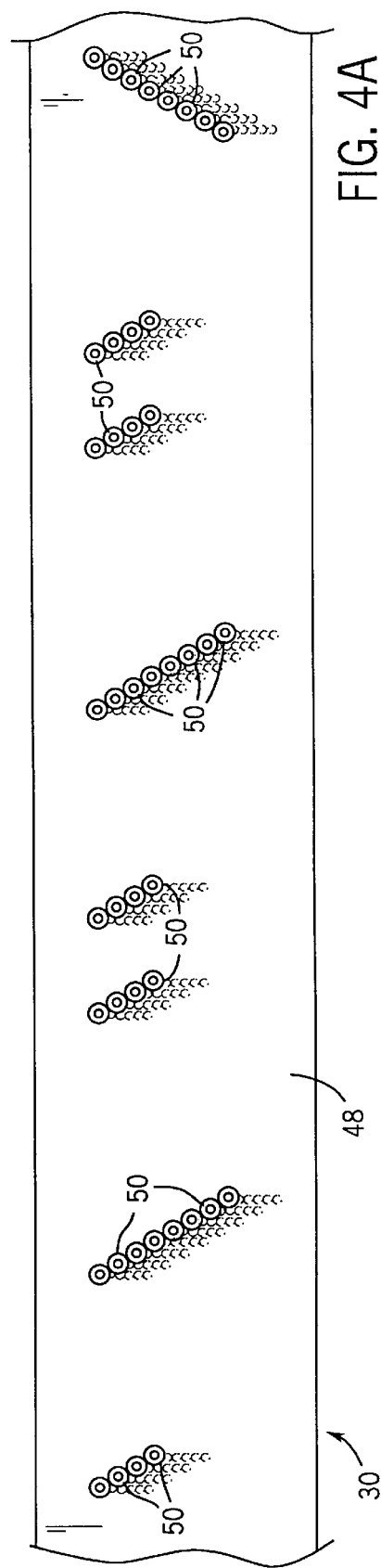
FIG. 4a is a view of the nozzle arrangement for the bead applicator as viewed from line 4A in FIG. 4.

The fabrication process as described thus far is able to produce nonwoven trilaminates at relatively high speeds for example 200–300 feet per minute machine speed or higher speeds. At such speeds, it is preferred to apply the through-bonding adhesive via an adhesive bead applicator 30. Referring to FIGS. 4 and 4a, the bead applicator 30 includes a substantially rectangular adhesive plenum 48 and a plurality of nozzles 50 extending downward from the plenum 48. The nozzles 50 are arranged as a plurality of diagonal rows (see FIG. 4a). In the embodiment shown in FIGS. 4 and 4a, there are eight (8) nozzles per each diagonal row. Other nozzle arrangements may be suitable.

Depending on the characteristics of the nonwoven web 12a and the particular through-bonding adhesive, it may or may not be desirable for the nozzles 50 to be in contact with the nonwoven web 12a when the nonwoven web 12a passes through the adhesive bead applicator 30 during machine operation. The through-bonding adhesive add-on rate required to bond through the inner elastomeric web 16a is directly related to the thickness of the elastomeric web 16a. If the elastomeric mesh web 16a is an elastomeric mesh material having a thickness of approximately 0.025 inches, the preferred add-on rate for through-bonding adhesive is approximately 1.75 mg/lineal inch/bead. The through-bonding adhesive should be applied to the nonwoven web 12a at a temperature sufficient to allow the adhesive to flow through the elastomeric layer 16a and wet out the second nonwoven web 18a at the speed in which the laminating machine is being operated. As mentioned, the preferred through-bonding adhesive is an oil resistant, polybutylene-based hot melt adhesive, such as that disclosed in copending U.S. patent application Ser. No. 08/632,117, now U.S. Pat. No. 6,008,148, and marketed by Ato Findley under the name H9282F. It is preferred that this particular adhesive be applied to the first nonwoven web 12a at a temperature of 320° F. when applied in the contact mode, and approximately 350–360° F. when applied in the non-contact mode.

The open time for the through-bonding adhesive between the bead applicator 30 and the compression nip 38 should be sufficiently short enough so that the beads of through-bonding adhesive do not cool significantly or solidify. The laminating machine 26 is operated effectively with an open time between the bead applicator 30 and the compression nip 38 of approximately 1 second or less, although depending on the materials used to fabricate the nonwoven trilaminate, it may be possible to have longer open times for the through-bonding adhesive beads.

FIG. 5 illustrates the adhesive layout across the trilaminate web 10a. The two rows of sprayed-on adhesive, which are sprayed on the second nonwoven web 18a and the combination of the elastomeric web 16a and the second nonwoven web 18a, are illustrated on FIG. 5 by reference numerals 52a, 52b. Each row includes 40 spirals as depicted in FIG. 5. Each of the spirals has a width of approximately ¾ of an inch. The rows 52a, 52b are each formed by staggered rows of 20 spirals. The staggered rows promotes full coverage of the sprayed-on adhesive.

The beads 50 of through-bonding adhesive are applied only in certain selected areas as shown in FIG. 5. FIG. 5 shows slit lines 54 in web 10a as well as perforation lines 56 in the web 10a. The beads 50 of through-bonding adhesive are applied only in the regions of the web 10a which are adjacent the perforation lines 56 and nearly adjacent the slit lines 54. In the preferred embodiment of the invention, the beads 50 in each group are spaced approximately 0.1 inches from one another. The application rate per bead is preferably 1.75 mg per inch as previously discussed. (Ato Findley Adhesive H9282F for beads and Ato Findley Adhesive H2120 or H9282F for spirals). By applying the beads 50 only at locations on the web 10a which are adjacent to perforation lines 56 and nearly adjacent the slit lines 54, the integrity of the finished product is improved inasmuch as the beads 50 serve to maintain the laminated structure, but the absence of the beads in the middle areas of each individual web (i.e., each individual web is defined by a respective slit line 54 and perforation line 56) prevents each individual web from becoming overly stiff and maintains relative softness of each individual web.

Peel strength tests were performed on samples of nonwoven trilaminated structures fabricated in accordance with the above described method, except that the adhesive applied in beads (50 in FIG. 5) was absent. The test results indicated that the average peel strength of through-bonding that occurs directly between the nonwoven outer layers 12, 18 is significantly greater than the average peel strength of any bonds that may be present directly between the elastomeric layer 16 and either of the outer nonwoven layers 12, 18. Samples were tested on an MTS tensile tester using a standard test at a constant crosshead speed of 12 inches per minute. The test results were compared to samples in which release paper was substituted for one of the nonwoven layers. It was necessary to run the peel tests without the adhesive applied in beads (50 in FIG. 5) because, otherwise, the peel tests destructed the nonwoven individual results for the samples having the release paper are given below.

TABLE 1

| Sample | Avg. Peel (g/in) |
| --- | --- |
| 1 | 119 |
| 2 | 156 |
| 3 | 148 |
| 4 | 147 |
| 5 | 153 |
| Overall Avg. | 144 |

The results for the nonwoven trilaminate samples (bead adhesive absent) are given in Table 2:

TABLE 2

| Sample | Avg. Peel (g/in) |
| --- | --- |
| 1 | 1708 |
| 2 | 1796 |
| 3 | 1332 |
| 4 | 1450 |
| 5 | 1485 |
| Overall Avg. | 1554 |

From the above peel strength test results, it is apparent that the average peel strength of the through-bonding that occurs directly between the nonwoven outer layers 12, 18 is significantly greater than average peel strength of any bonds that may be presently directly between the inner layer 16 and either of the outer nonwoven layers 12, 18. In addition, the application of bead adhesive (50 in FIG. 5) as is desired in accordance with the preferred embodiment of the invention increases the peel strength above the results shown in Table 2. It should therefore be apparent to those skilled in the art that using a high strength through-bonding technique in accordance with the invention can greatly improve the integrity and durability of nonwoven trilaminates.

The invention has been described in conjunction with a preferred embodiment of carrying out the invention, however, the invention may be implemented in modified form without departing from the true scope or spirit of the invention. For example, the operating parameters (e.g., adhesive application rate, adhesive application method, adhesive application temperature, machine speed, adhesive viscosity, adhesive open time before compression, etc.) may vary substantially depending on the specific application. These parameters should be optimized not only to maintain integrity of the finished product, but also to maintain the integrity of the laminated structure during subsequent processing, handling and packaging. The scope of the invention should be determined in light of the following claims.

We claim:

1. A multi-layer laminated structure comprising: a first layer of breathable material having a first bonding side; a second layer of breathable material having a second bonding side; an elastomeric web layer having a plurality of openings therethrough, the elastomeric web layer being laminated between the first layer of breathable material and the second layer of breathable material to form a multi-layer laminate structure, the elastomeric web layer being stretchable in at least one dimension, each of said first layer, second layer and elastomeric web layer having opposite edges extending longitudinally in the machine direction and a middle area between said opposite edges; and through-bonding adhesive that through-bonds the first and second layers of breathalbe materal to each other through the openings in the inner elastomeric web layer, said through-bonding adhesive disposed on the first bonding side of said first layer only at a location adjacent to the opposite edges of said first layer and leaving said middle area of said first layer free of said through-bonding adhesive, wherein an average peel strength of the through-bonding that occurs directly between the layers of breathable material is substantially greater than the average peel strength of any bonds that may be present directly between the elastomeric layer and either layer of breathable material such that the through-bonding directly between the layers of breathable material comprises the primary bond to maintain said multi-layer laminate structure so that the elastomeric web is mechanically secured within the multi-layer laminate structure via the through-bonding which occurs directly between the layers of breathable material, and further wherein the through-bonding adhesive is chemically resistant to processing aids in the elastomeric web layer.

2. A multi-layer laminated structure as recited in claim 1 wherein the elastomeric web layer is stretchable in two dimensions.

3. A multi-layer laminated structure as recited in claim 1 wherein the layers of breathable material are layers of nonwoven material which do not stretch in a machine direction and are spreadable in a cross direction that is substantially perpendicular to the machine direction.

4. A multi-layer laminated structure as recited in claim 1 wherein the through-bonding adhesive is an oil resistant, polybutylene-based hot melt adhesive.

5. A multi-layer laminated structure as recited in claim 1 further comprising a sprayed-on adhesive disposed on the second bonding side of said second layer that bonds said second layer of breathable material directly to the elastomeric web layer.

6. A multi-layer laminated structure as recited in claim 1 wherein the layers of breathable material are outer layers of a trilaminate structure and the elastomeric web layer is an inner layer of the trilaminate web structure.

7. A nonwoven trilaminate structure as recited in claim 6 wherein the outer layers of breathable material are layers of nonwoven material.

8. A multi-layer laminated structure comprising:
a first layer of breathable material having a first bonding side;
a second layer of breathable material having a second bonding side;
an elastomeric web layer having a plurality of openings therethrough, the elastomeric web layer being laminated between the first layer of breathable material and the second layer of breathable material to form a multi-layer laminate structure, the elastomeric web layer being stretchable in at least one dimension, each of said first layer, second layer and elastomeric web layer having opposite edges extending longitudinally in the machine direction and a middle area between said opposite edges;

through-bonding adhesive that through-bonds the first and second layers of breathable material to each other through the openings in the inner elastomeric web layer, wherein the through-bonding adhesive is chemically resistant to processing aids in the elastomeric web, and said multi-layer, laminated structure includes a plurality of alternately spaced parallel perforation lines and slit lines extending longitudinally in the machine direction, said through-bonding adhesive disposed on the first bonding side of said first layer only at a location adjacent to said perforation lines and nearly adjacent to said slit lines and leaving said middle area therebetween free of said through-bonding adhesive, wherein an average peel strength of the through-bonding that occurs directly between the layers of breathable material is more than two times greater than the average peel strength of any bonds that may be present directly between the elastomeric layer and either layer of breathable material such that the elastomeric web layer is mechanically secured within the multi-layer laminate structure via the through-bonding which occurs directly between the layers of breathable material.

9. A multi-layer laminated structure as recited in claim 8 wherein the elastomeric web layer is stretchable in two dimensions.

10. A multi-layer laminated structure as recited in claim 8 wherein the layers of breathable material are layers of nonwoven material which do not stretch in a machine direction and are spreadable in a cross direction that is substantially perpendicular to the machine direction.

11. A multi-layer laminated structure as recited in claim 8 wherein the through-bonding adhesive is an oil resistant, polybutylene-based hot melt adhesive.

12. A multi-layer laminated structure as recited in claim 8 further comprising a sprayed-on adhesive disposed on the second bonding side of said second layer that bonds said second layer of breathable material directly to the elastomeric web layer.

13. A multi-layer laminated structure as recited in claim 8 wherein the layers of breathable material are outer layers of a trilaminate structure and the elastomeric web layer is an inner layer of the trilaminate web structure.

14. A nonwoven trilaminate structure as recited in claim 13 wherein the outer layers of breathable material are layers of nonwoven material.

15. A multi-layer laminated structure comprising: a first layer of breathable material having a first bonding side; a second layer of breathable material having a second bonding side; an elastomeric web layer having a plurality of openings therethrough, the elastomeric web layer being laminated between the first layer of breathable material and the second layer of breathable material to form a multi-layer laminate structure, the elastomeric web layer being stretchable in at least one dimension, each of said first layer, second layer and elastomeric web layer having opposite edges extending longitudinally in the machine direction and a middle area between said opposite edges; and through-bonding adhesive that through-bonds the first and second layers of breathalbe materal to each other through the openings in the inner elastomeric web layer, said through-bonding adhesive disposed on the first bonding side of said first layer only at a location adjacent to the opposite edges of said first layer and leaving said middle area of said first layer free of said through-bonding adhesive, wherein an average peel strength of the through-bonding that occurs directly between the layers of breathable material is more than two times greater than the average peel strength of any bonds that may be present directly between the elastomeric layer and either layer of breathable material such that the through-bonding directly between the layers of breathable material comprises the primary bond to maintain said multi-layer laminate structure so that the elastomeric web is mechanically secured within the multi-layer laminate structure via the through-bonding which occurs directly between the layers of breathable material, and further wherein the through-bonding adhesive is chemically resistant to processing aids in the elastomeric web layer.

16. A multi-layer laminated structure as recited in claim 15 wherein the elastomeric web layer is stretchable in two dimensions.

17. A multi-layer laminated structure as recited in claim 15 wherein the layers of breathable material are layers of nonwoven material which do not stretch in a machine direction and are spreadable in a cross direction that is substantially perpendicular to the machine direction.

18. A multi-layer laminated structure as recited in claim 15 wherein the through-bonding adhesive is an oil resistant, polybutylene-based hot melt adhesive.

19. A multi-layer laminated structure as recited in claim 15 further comprising a sprayed-on adhesive disposed on the second bonding side of said second layer that bonds said second layer of breathable material directly to the elastomeric web layer.

20. A multi-layer laminated structure as recited in claim 15 wherein the layers of breathable material are outer layers of a trilaminate structure and the elastomeric web layer is an inner layer of the trilaminate web structure.

21. A nonwoven trilaminate structure as recited in claim 21 wherein the outer layers of breathable material are layers of nonwoven material.

22. A multi-layer laminated structure comprising: a first layer of breathable material having a first bonding side; a second layer of breathable material having a second bonding side; an elastomeric web layer having a plurality of openings therethrough, the elastomeric web layer being laminated between the first layer of breathable material and the second layer of breathable material to form a multi-layer laminate structure, the elastomeric web layer being stretchable in at least one dimension, each of said first layer, second layer and elastomeric web layer having opposite edges extending longitudinally in the machine direction and a middle area between said opposite edges; and through-bonding adhesive that through-bonds the first and second layers of breathalbe materal to each other through the openings in the inner elastomeric web layer, said through-bonding adhesive disposed on the first bonding side of said first layer only at a location adjacent to the opposite edges of said first layer and leaving said middle area of said first layer free of said through-bonding adhesive, wherein an average peel strength of the through-bonding that occurs directly between the layers of breathable material is more than ten times greater than the average peel strength of any bonds that may be present directly between the elastomeric layer and either layer of breathable material such that through-bonding directly between the layers of breathable material comprises the primary bond to maintain said multi-layer laminate structure so that the elastomeric web is mechanically secured within the multi-layer laminate structure via the through-bonding which occurs directly between the layers of breathable material, and further wherein the through-bonding adhesive is chemically resistant to processing aids in the elastomeric web layer.

23. A multi-layer laminated structure as recited in claim 22 wherein the elastomeric web layer is stretchable in two dimensions.

24. A multi-layer laminated structure as recited in claim 22 wherein the layers of breathable material are layers of nonwoven material which do not stretch in a machine direction and are spreadable in a cross direction that is substantially perpendicular to the machine direction.

25. A multi-layer laminated structure as recited in claim 22 wherein the through-bonding adhesive is an oil resistant, polybutylene-based hot melt adhesive.

26. A multi-layer laminated structure as recited in claim 22 further comprising a sprayed-on adhesive disposed on the second bonding side of said second layer that bonds said second layer of breathable material directly to the elastomeric web layer.

27. A multi-layer laminated structure as recited in claim 22 wherein the layers of breathable material are outer layers of a trilaminate structure and the elastomeric web layer is an inner layer of the trilaminate web structure.

28. A nonwoven trilaminate structure as recited in claim 22 wherein the outer layers of breathable material are layers of nonwoven material.

* * * * *